United States Patent
Lee et al.

(10) Patent No.: US 11,684,547 B2
(45) Date of Patent: Jun. 27, 2023

(54) FLUID BAG ADAPTOR

(71) Applicant: EPIC MEDICAL PTE LTD, Singapore (SG)

(72) Inventors: Freddie Eng Hwee Lee, Singapore (SG); Withawin Wongdee, A. Sriracha Chonburi (TH)

(73) Assignee: EPIC MEDICAL PTE. LTD., Singapore (SG)

( * ) Notice: Subject to any disclaimer, the term of this patent is extended or adjusted under 35 U.S.C. 154(b) by 339 days.

(21) Appl. No.: 16/796,013

(22) Filed: Feb. 20, 2020

(65) Prior Publication Data
US 2020/0268609 A1 Aug. 27, 2020

Related U.S. Application Data

(60) Provisional application No. 62/808,891, filed on Feb. 22, 2019.

(51) Int. Cl.
| | | |
|---|---|---|
| A61J 1/20 | (2006.01) | |
| A61M 39/10 | (2006.01) | |
| A61J 1/10 | (2006.01) | |
| A61J 1/14 | (2023.01) | |

(52) U.S. Cl.
CPC ............ *A61J 1/2048* (2015.05); *A61J 1/10* (2013.01); *A61J 1/1475* (2013.01); *A61J 1/201* (2015.05); *A61J 1/2055* (2015.05); *A61M 39/10* (2013.01)

(58) Field of Classification Search
CPC ........ A61J 1/1475; A61J 1/2048; A61J 1/201; A61J 1/2055; A61J 1/2065; A61J 1/1481; A61J 1/10; A61M 39/10
See application file for complete search history.

(56) References Cited

U.S. PATENT DOCUMENTS

| | | | |
|---|---|---|---|
| 3,990,727 A | | 11/1976 | Gallagher |
| 4,013,310 A | * | 3/1977 | Dye ........................ F16L 37/05 |
| | | | 285/423 |
| 5,688,254 A | | 11/1997 | Lopez et al. |
| 7,670,326 B2 | * | 3/2010 | Shemesh ............... A61J 1/2096 |
| | | | 604/414 |
| 2006/0149211 A1 | | 7/2006 | Simpson et al. |
| 2013/0158521 A1 | | 6/2013 | Sobue |
| 2014/0188087 A1 | * | 7/2014 | Griesbach, III .... A61J 15/0026 |
| | | | 604/536 |
| 2015/0359709 A1 | * | 12/2015 | Kriheli .................. A61J 1/2048 |
| | | | 604/405 |
| 2019/0046410 A1 | * | 2/2019 | Shemesh ............... A61J 1/2096 |

FOREIGN PATENT DOCUMENTS

| | | |
|---|---|---|
| EP | 3299060 A1 | 3/2018 |
| WO | WO 2016/210300 A1 | 12/2016 |

OTHER PUBLICATIONS

Merriam-Webster "noose", https://www.merriam-webster.com/dictionary/noose, accessed Mar. 9, 2022, published Jun. 3, 2017. (Year: 2017).*
European Patent Application No. 20157033.0; Extended Search Report; dated Oct. 9, 2020; 8 pages.

\* cited by examiner

*Primary Examiner* — Ariana Zimbouski
(74) *Attorney, Agent, or Firm* — BakerHostetler

(57) ABSTRACT

An adaptor including a hub and a connector, the hub having an exterior surface and an interior surface, the interior surface defining a first cavity; and the connector including: a noose and at least one slider coupled to the noose, the slider being configured to engage the exterior surface such that the noose is received by the first cavity.

17 Claims, 12 Drawing Sheets

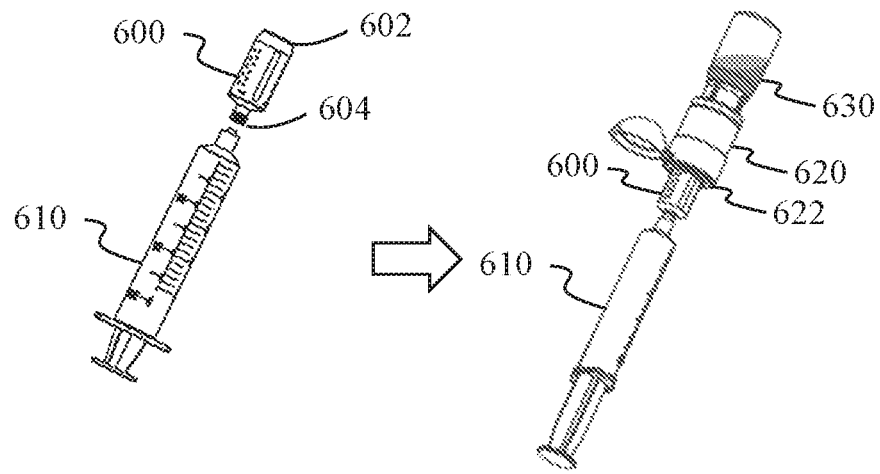
FIG. 10A
FIG. 10B
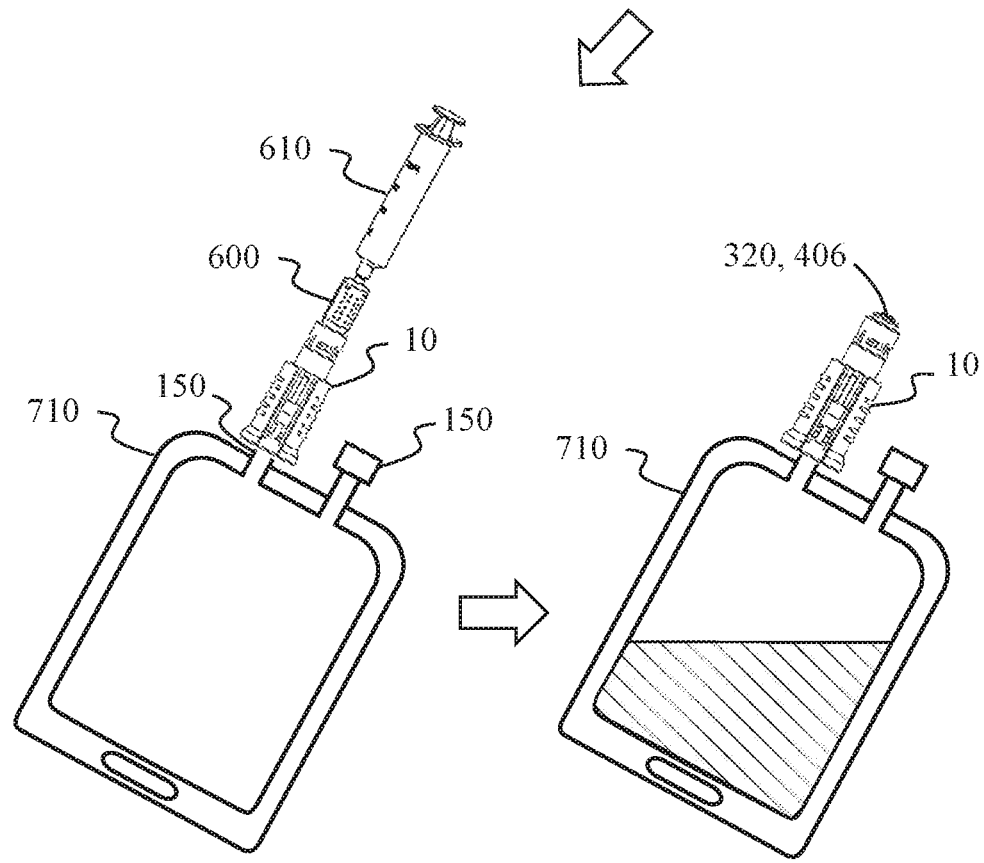
FIG. 10C
FIG. 10D

FLUID BAG ADAPTOR

CROSS-REFERENCE TO RELATED APPLICATIONS

This claims priority to U.S. Patent Application Ser. No. 62/808,891 filed Feb. 22, 2019, the disclosure of which is hereby incorporated by reference as if set forth in its entirety herein.

TECHNICAL FIELD

The present disclosure relates generally to medical devices and, more particularly, to adaptors for fluid bags.

BACKGROUND

A typical fluid bag, such as one for infusion use, has one port (inlet port) for administering fluid into the fluid bag and another port (outlet port) that allows contents of the fluid bag to be infused to a patient by means of an administration set attached. The inlet ports are typically designed with a pliable septum through which medication could be administered by a syringe and needle. Depending on the seal ability of such membranes/septum, the process of administering medication could leave traces of medication as the needle is pulled out. In general, spillage and needle stick injuries also contribute to the issues associated with unsafe handling. Risks associated with delivery of hazardous drugs from their original containers to patients have been extensively studied and the impact on healthcare personnel due to issues of exposure to hazardous medication is unequivocally well known. Malformations, spontaneous abortions and still births have been associated with exposures to cytostatic agents. Background personnel and visitors in open wards are also exposed to environmental contaminants due to the escape of hazardous drug or vapor concentrations and also in surface contamination. The enforcement of safety standards, e.g., the United States Pharmacopeia (USP) General Chapter 800 that relates to safe handling of hazardous drugs, confirm the gravity of the issues if left unregulated. There is therefore a need for apparatus and methods that promote safer transfer of hazardous medication into fluid bags or such containers that are commonly used in a hospital setting.

SUMMARY

To address such needs, embodiments of the present invention are described below. In one aspect, the present application discloses an adaptor comprising a hub and a connector, the hub having an exterior surface and an interior surface, the interior surface defining a first cavity; the connector including: a noose and at least one slider coupled to the noose, the noose being receivable by the first cavity when the at least one slider engages the exterior surface.

The adaptor may be further characterised in that the connector is elastically deformable or elastically deformed by engagement of the at least one slider with the exterior surface such that the at least one slider is biased against the exterior surface. The hub further includes at least one ramp extending in an axial direction, the exterior surface being disposed on the at least one ramp such that the connector is increasingly deformed as the connector is displaced in the axial direction relative to the hub. The at least one slider and the exterior surface are configured to ratchetly engage with one another to prevent movement of the connector relative to the hub in a direction substantially opposing the axial direction. The hub further defines a second cavity, the second cavity extending from a divider to an opposing end, wherein the second cavity is in fluid communication with the first cavity at the divider, and wherein the second cavity is sealable at the opposing end by a hub septum. The adaptor further includes a needle axially disposed in the hub, and wherein fluid communication between the first cavity and the second cavity is solely via the needle. Adapted for use with a fluid bag having a port, the port being coupled with a port septum, the adaptor is characterised in that the noose is configured to elastically couple the port and to position the port septum in the first cavity for piercing by the needle, such that fluid communication between the second cavity and the port is solely via the needle.

In another aspect, the adaptor includes a hub and a connector, the hub having an exterior surface and an interior surface, the interior surface defining a first cavity; the connector including: a noose and at least one slider coupled to the noose, the noose being receivable by the first cavity when the at least one slider engages the exterior surface; wherein the connector is elastically deformable or elastically deformed by engagement of the at least one slider with the exterior surface such that the at least one slider is biased against the exterior surface; and the hub further includes two slots diametrically disposed on the hub and extending in an axial direction; and two pairs of ramps, each pair of ramps flanking one of the two slots respectively, wherein the exterior surface is disposed on the pairs of ramps.

The adaptor may be further characterised in that the connector is increasingly deformed as the connector is displaced in the axial direction relative to the hub. The exterior surface includes a plurality of ramp teeth disposed at increasing ramp heights, the plurality of ramp teeth being configured to ratchetly engage with a corresponding slider to prevent movement of the connector relative to the hub in a direction substantially opposing the axial direction, the corresponding slider being one of the at least one slider. The connector may include two sliders, wherein the connector is deformable by the noose being extended diametrically across the first cavity such that each pair of ramps is in biased engagement with a corresponding slider, the corresponding slider being one of the two sliders. The hub further defines a second cavity, the second cavity extending from a divider to an opposing end, wherein the second cavity is in fluid communication with the first cavity at the divider, and wherein the second cavity is sealable at the opposing end by a hub septum. The adaptor further includes a needle axially disposed in the hub, and wherein fluid communication between the first cavity and the second cavity is solely via the needle.

In another aspect, a fluid transfer system includes a fluid bag and an adaptor; the fluid bag having a port sealed with a port septum; and the adaptor including: a hub defining a first cavity and a second cavity, the second cavity extending from a divider to an opposing end, the opposing end being sealable by a hub septum; a needle disposed in the hub at the divider; and a connector having a noose, the noose being configured to couple the port and to present the port septum in the first cavity for piercing by the needle, such that fluid communication between the port and the second cavity is solely via the needle. The noose is configured to bias the connector in ratchet engagement with the hub against decoupling of the adaptor and the port when the second cavity and the port are in fluid communication.

BRIEF DESCRIPTION OF DRAWINGS

FIGS. 10A to 10D illustrate a fluid transfer system and method according to one embodiment of the present disclosure.

DETAILED DESCRIPTION

It will be readily understood that the components of the embodiments, as generally described and illustrated in the figures herein, may be arranged and designed in a wide variety of different configurations in addition to the described example embodiments. Thus, the following more detailed description of the example embodiments, as represented in conjunction with the figures, is not intended to limit the scope of the embodiments, as claimed, but is merely representative of example embodiments.

Reference throughout this specification to "one embodiment", "another embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, that the various embodiments be practiced without one or more of the specific details, or with other methods, components, materials, etc. In other instances, some or all known structures, materials, or operations may not be shown or described in detail to avoid obfuscation.

Figure 1:
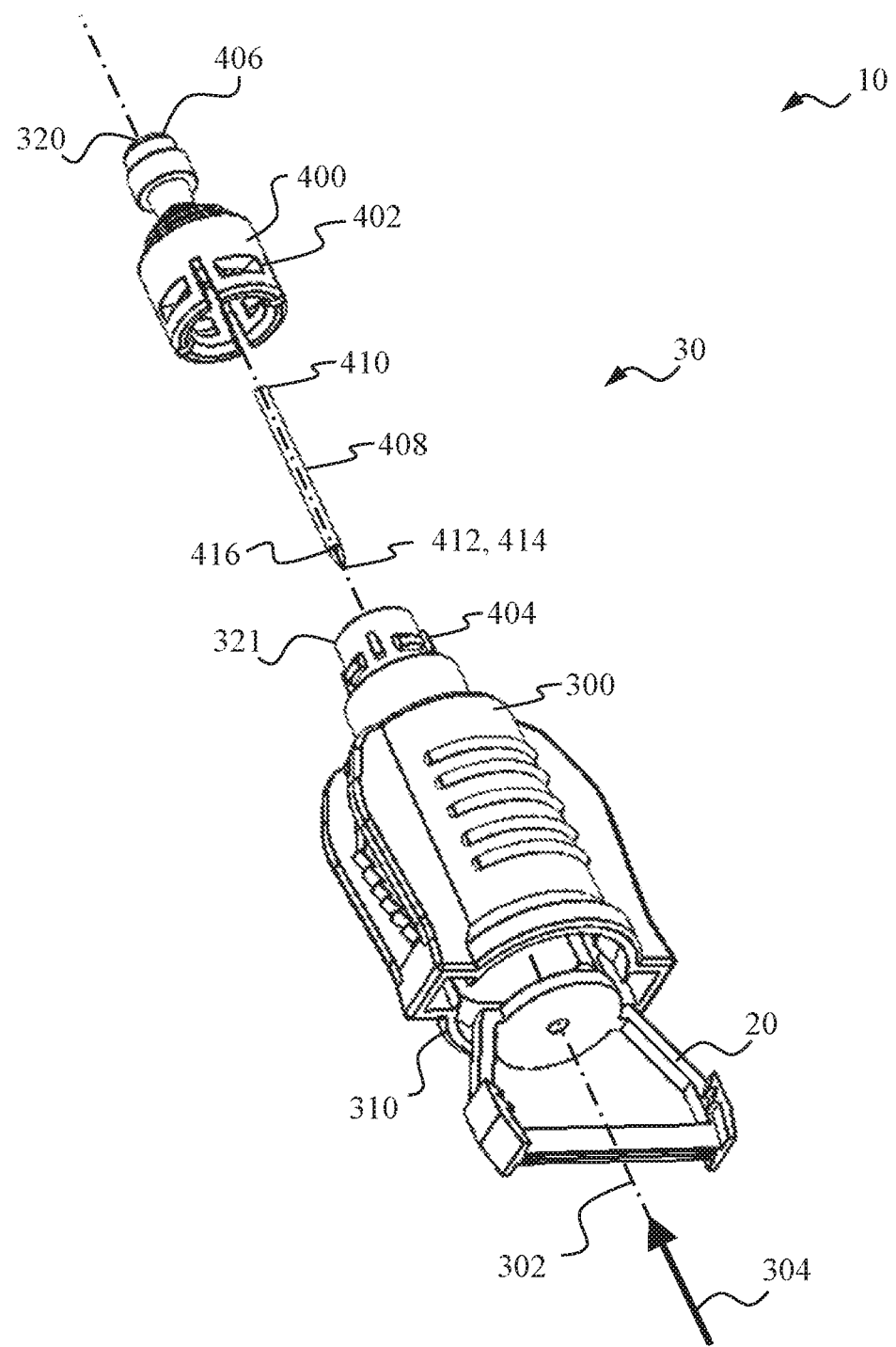
FIG. 1 is an exploded view of an adaptor in accordance with an embodiment of the present disclosure.

FIG. 1 is an exploded view of an adaptor 10 in accordance with an embodiment of the present disclosure. The adaptor 10 includes a connector 20 and a hub 30. The hub 30 defines an axial direction 304 extending from a first end 310 of the hub 30 to a second end 320 of the hub 30. The hub 30 may be provided with a housing 300 and a cap 400. The cap 400 may include locking features 402 for coupling with complementary features 404 of the housing 300. The cap 400 may further include a hub septum 406 configured for engaging with a compatible connecting interface of a delivery system 40. Locking features 402 may be provided on the cap 400 for engagement with the complementary features 404 on the housing 300 to prevent de-coupling of the cap 400 from the housing 300.

Figure 2A:
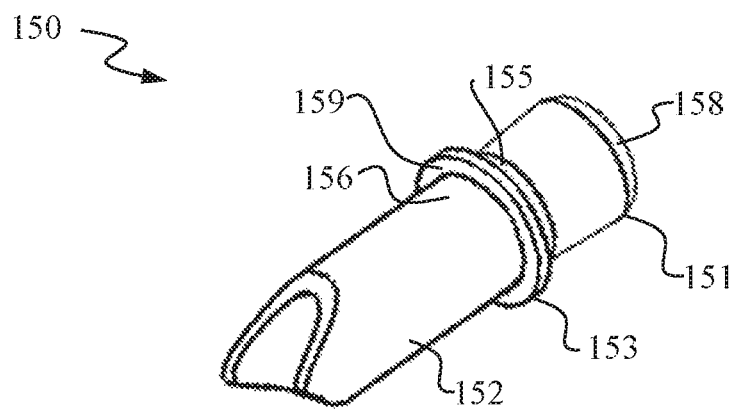
FIG. 2A is a partial perspective view of a port of a fluid bag.
Figure 2B:
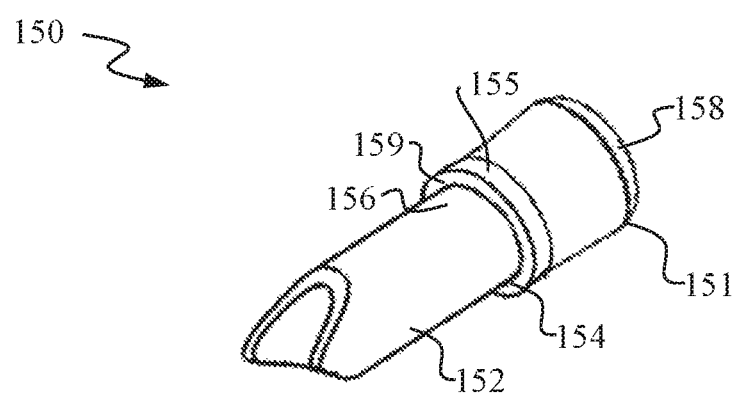
FIG. 2B is a partial perspective view of a port of another fluid bag.

The adaptor 10 is suitable for use with fluid bags. References in this document to "fluid bags" will be understood to include fluid bags such as those for infusion use, as well as other containers commonly used in a hospital setting. Fluid bags are available in different forms. Different types of fluid bags may have inlet ports and outlet ports of different types and dimensions. The adaptor 10 is configured to be suitable for use with different types of fluid bags having various forms of ports. To aid understanding, a port 150 of a fluid bag is shown in FIG. 2A as an example of an inlet port of a fluid bag. The port 150 includes a tube 152 with an inlet at a terminal 151. The port 150 may be fitted with a port septum 158 over the inlet. Near the inlet, the port 150 may be provided with a flange 153 having a larger diameter than adjacent parts 155, 156 of the tube 152. The flange 153 provides a ledge 159 or a shoulder substantially facing away from the terminal 151. In some other cases, as shown in FIG. 2B, the tube 152 may have a constriction 154 having a smaller external diameter relative to an adjacent part 155 of the tube 152. The constriction 154 also provides a ledge 159 or a shoulder substantially facing away from the terminal 151.

Figure 3:
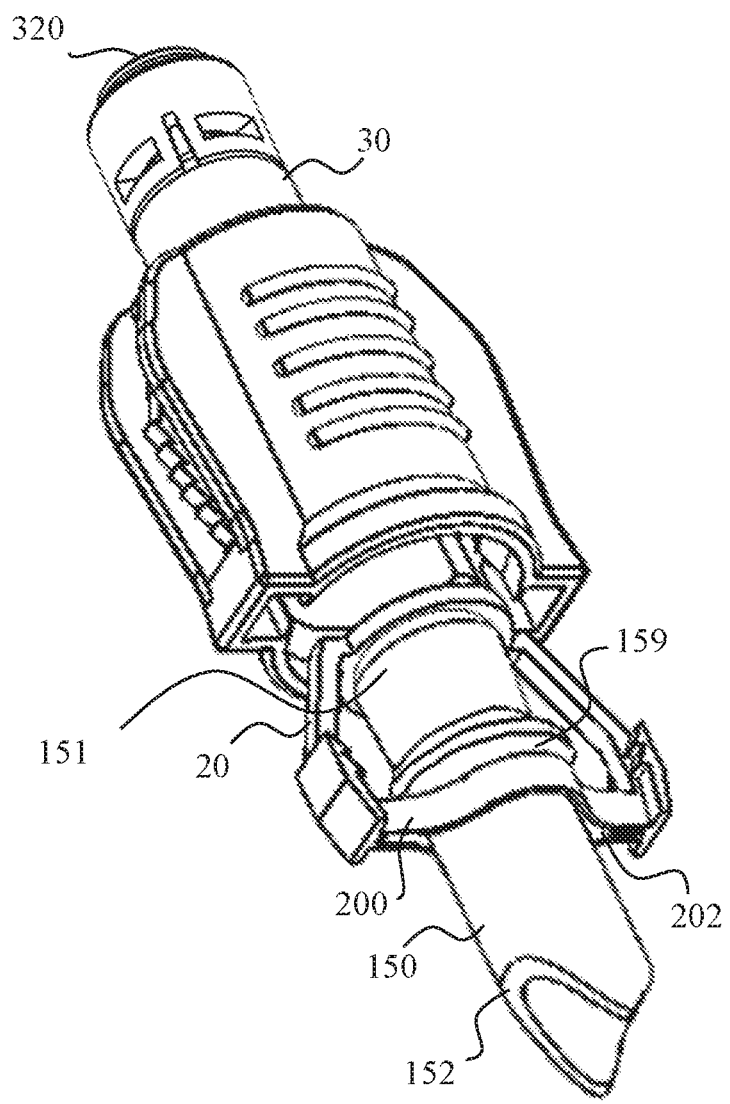
FIG. 3 is a perspective view of a port coupled to a connector, according to one embodiment of the present disclosure.
Figure 11:
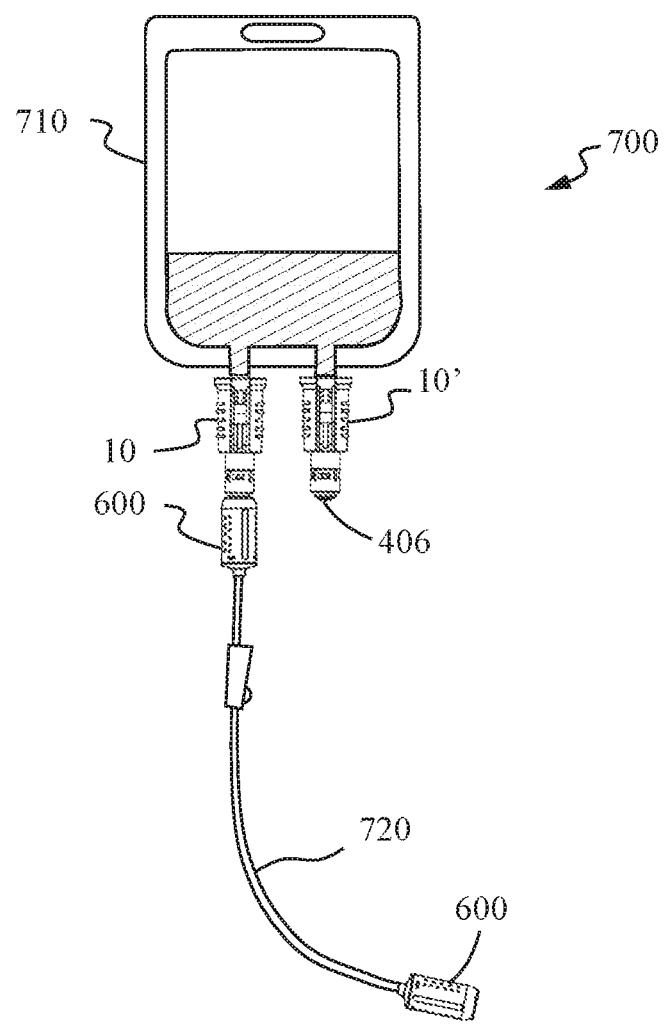
FIG. 11 illustrates another fluid transfer system according to another embodiment of the present disclosure.

Referring now to FIG. 3, in assembly, a hub 30 of the adaptor 10 and a connector 20 of the adaptor 10 are aligned axially for assembly so that the hub 30 and the connector 20 are configured for slidable engagement. The connector 20 is shown here coupled to a port 150 so that, in assembly, the port 150 is also axially aligned with the adaptor 10. The connector 20 includes a noose 200 defining an opening 202. In one configuration, the opening 202 may be smaller or narrower than the tube 152. The noose 200 is resiliently deformable so that the size and shape of the opening 202 may receive the port 150 therethrough as shown. At least a part of the noose 200 conforms to the tube 152 and resiliently engages the port 150. The noose 200 is thus configured to resiliently or elastically couple the port 150. The provision of the noose 200 with a variable opening 202 enables the connector 20 to accommodate a range of ports 150 having tubes 152 of different diameters and shapes or configurations. Similarly, the connector 20 is also suitable for use with a range of ports 150 with differently sized and shaped terminals 151. Inadvertent de-coupling of the connector 20 from the port 150 is unlikely, for example, it is unlikely that the connector 20 would slip off the port 150. The ledge 159 of the flange 153 (or as the case may be, the ledge 159 of the constriction 154) will prevent such slippage or de-coupling. In such manner, the connector 20 (and accordingly, the adaptor 10) can accommodate dimensional variations in the port 150, and be used with various types of fluid bags having inlet ports of different dimensions, surface configurations, shapes, or other aspects. The adaptor 10 may be adapted for use with an outlet port of the fluid bag (FIG. 11)

Figure 4:
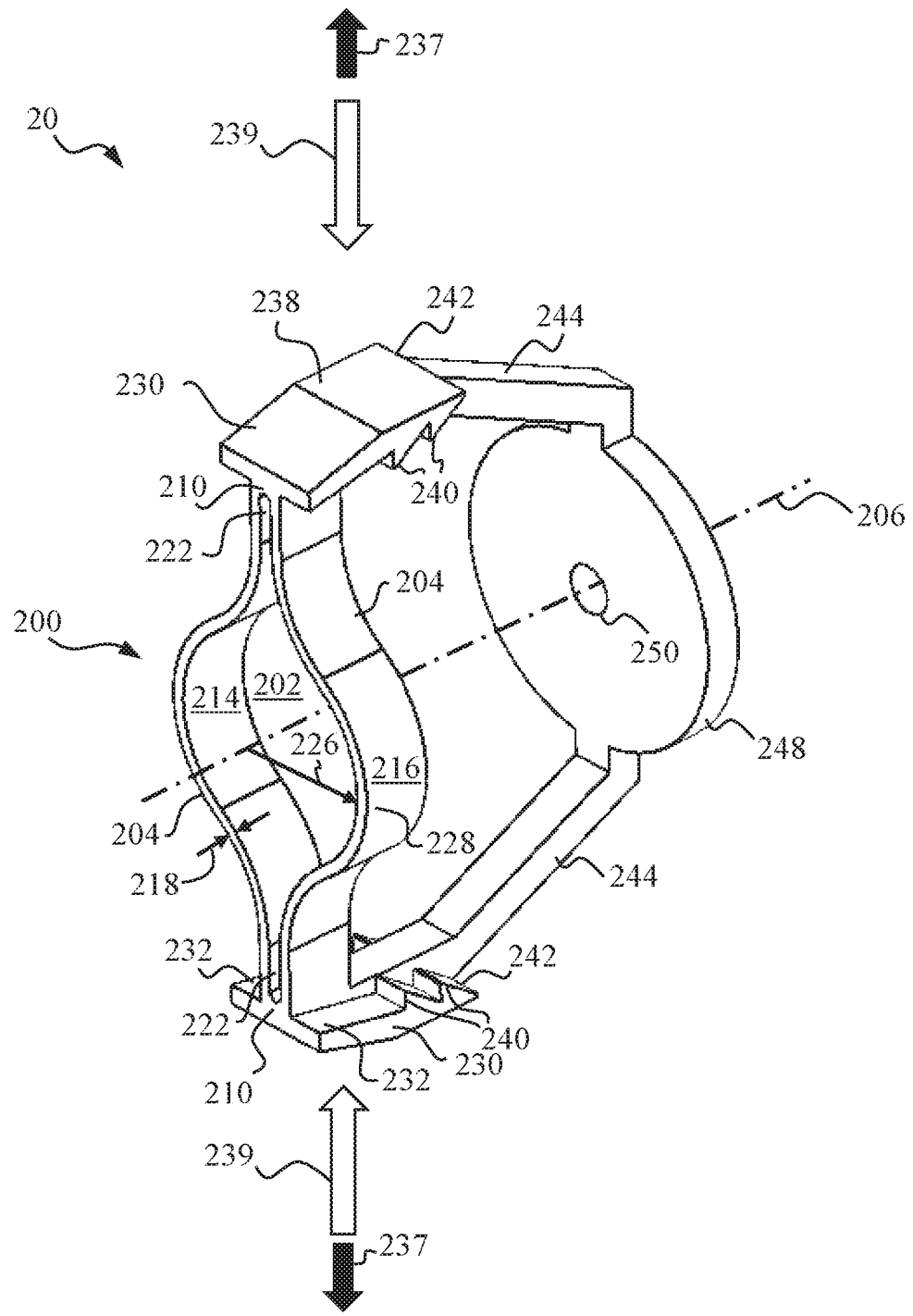
FIG. 4 is a perspective view of the connector of FIG. 1.
Figure 5A:
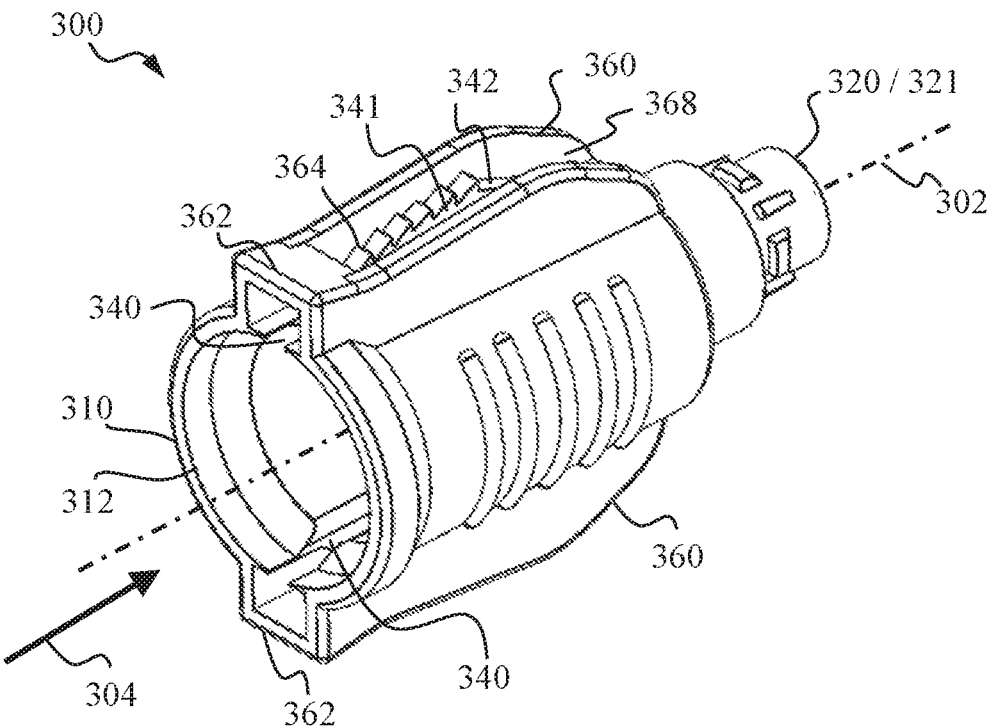
FIG. 5A is a perspective view of a housing of FIG. 1.
Figure 5B:
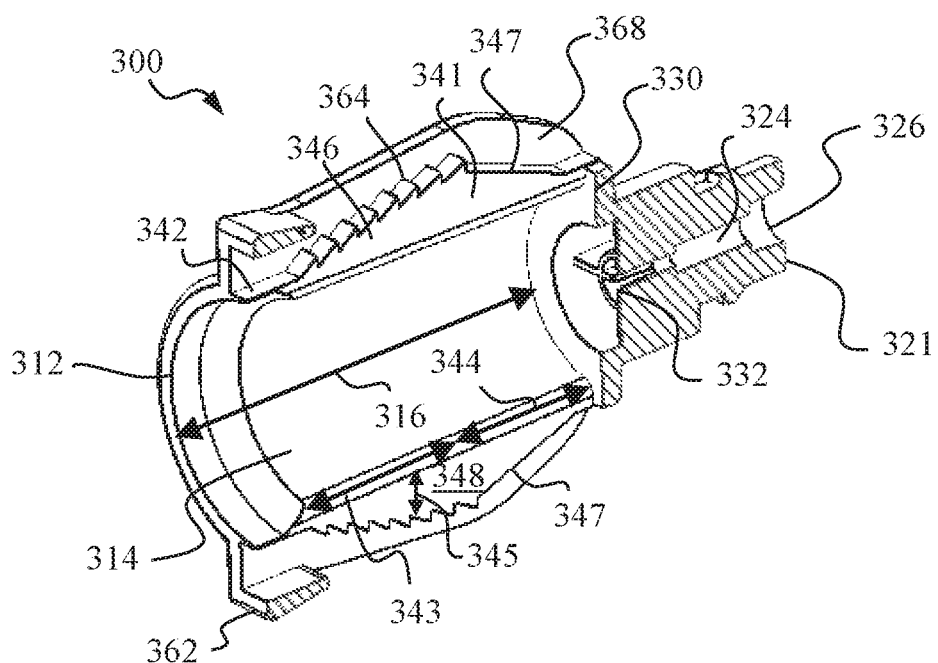
FIG. 5B is a cross-sectional view of the housing of FIG. 5A.
Figure 5C:
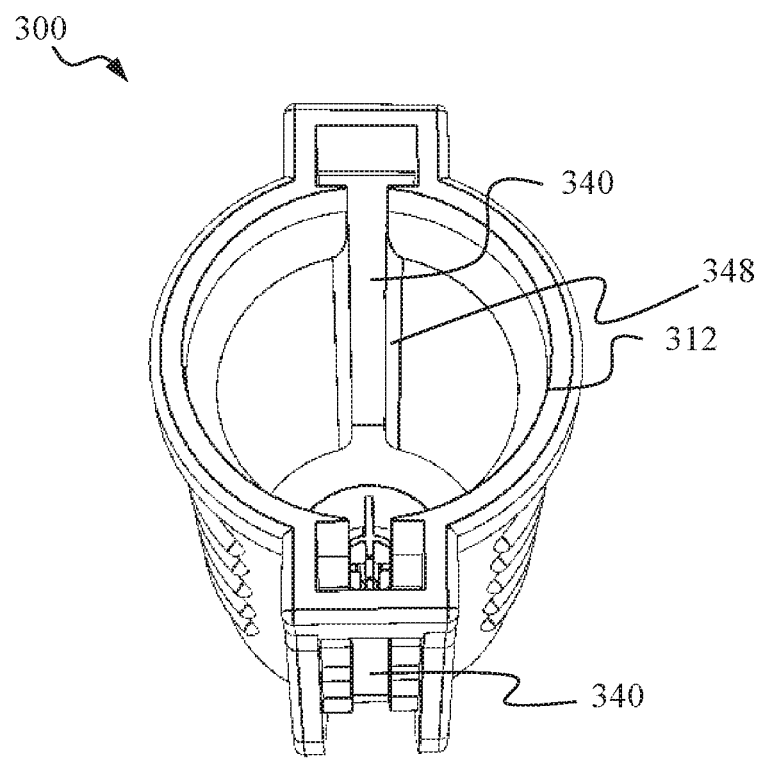
FIG. 5C is another perspective view of the housing of FIG. 5A.
Figure 5D:
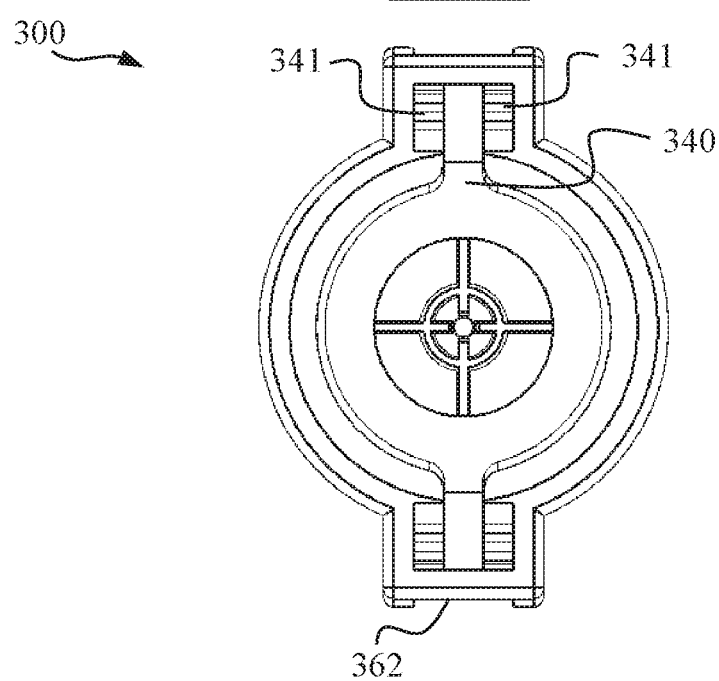
FIG. 5D is a side view of the housing of FIG. 5A.

The connector 20 is shown in greater detail in FIG. 4. The connector 20 may be described as a noose 200, a base 248, and two arms 244, each arm 244 extending from the noose 200 to the base 248. The noose may also be described as two bands 204 meeting at a neck 210. In this example, the noose 200 includes a pair of bands 204 with ends meeting at two diametrically opposed necks 210. Each neck 210 may include one end each of the two bands 204. The neck 210 may further include two ends of the bands 204 spaced apart to define a groove 222 extending in a radial direction relative to a first axis 206. The bands 204 are elastically or resiliently deformable, such that when the necks 210 are brought closer to one another by forces 239 for example, the bands 204 are flexed or curved to enlarge or widen the opening 202 between the bands 204. When the necks 210 are moved further apart from each other such as by forces 237 for example, the opening 202 between the bands 204 tend to shrink or narrow down. The noose 200 may be said to be characterized by a radius of curvature 226 defined as a linear dimension extending radially from the first axis 206 to a mid-point 228 of one of the bands 204. The noose 200 may be characterized by a larger radius of curvature 226 when the necks 210 are brought closer to the first axis 206. The noose may be characterized by a smaller radius of curvature 226 when the necks 210 are displaced away from one another or away from the first axis 206. The noose may be characterized by a larger radius of curvature 226 when the necks 210 are displaced toward one another or toward the first axis 206. Each band 204 may be configured to be less stiff in bending about an axis substantially parallel to the first axis 206, the first axis being one about which the connector 20 is configured with rotational symmetry. In one example, the desired deformation behavior of the bands 204 may be achieved by providing each band 204 with a substantially planar body having a first surface 214 and a generally opposing second surface 216 separated by a thickness 218, in which the thickness 218 is substantially smaller than the breadth of the band.

The connector 20 may further include a slider 230. In this example, the connector 20 includes a pair of diametrically opposed sliders 230 located at the necks 210. Each slider 230 may further include one or more tab surfaces 238. Part of the slider 230 may be bent towards the first axis 206. Part of the slider 230 may include one or more slider teeth 240. An interface 232 is provided with at least one slider tooth 240 projecting away from a leading edge 242 of the slider 230. The tab surface 238 may generally oppose the interface 232. In the example shown, the interface 232 is divided by the neck 210 and the arm 244.

The base 248 of the connector 20 may be substantially annular, with an outer diameter smaller than the separation between the two sliders 230. The base 248 is further configured with an aperture 250 coincidental with the first axis 206. The arms 244 may extend from the base 248 both radially and axially to join with the sliders 230, which together with the noose 200, contribute to the connector 20 being resiliently deformable.

The hub 30 includes a housing 300 which will be described with reference to FIG. 5A to FIG. 5D. The hub 30 defines a hub axis 302 extending axially from a first end 310 of the hub 30 to a second end 320 of the hub 30. The first end 310 defines a first housing opening 312 that leads to a first cavity 314. The axial direction 304 running from the first end 310 to the second end 320 is substantially parallel to the hub axis 302. From the first end 310, the first cavity 314 extends in the axial direction 304 for a first cavity length 316 before meeting a divider 330. The first cavity 314 communicates with a second cavity 324 through a divider aperture 332 in the divider 330. The second cavity 324 extends from the divider 330 in the axial direction 304 to a second housing opening 326 at an opposing end 321 of the housing 300. The hub 30 thus defines a first cavity 314 and a second cavity 324. The second cavity 324 extends from the divider 330 to the opposing end 321. Fluid communication between the first cavity 314 and the second cavity 324 is by way of the divider aperture 332 That is to say, the second cavity 324 is in fluid communication with the first cavity 314 at the divider 330. The second cavity 324 is sealable at the opposing end 321 by the hub septum 406. A needle 408 may be disposed at the divider 330 in the hub 30, for example, such that fluid communication between the first cavity 314 and the second cavity 324 is solely via the needle 408.

Figure 7B:
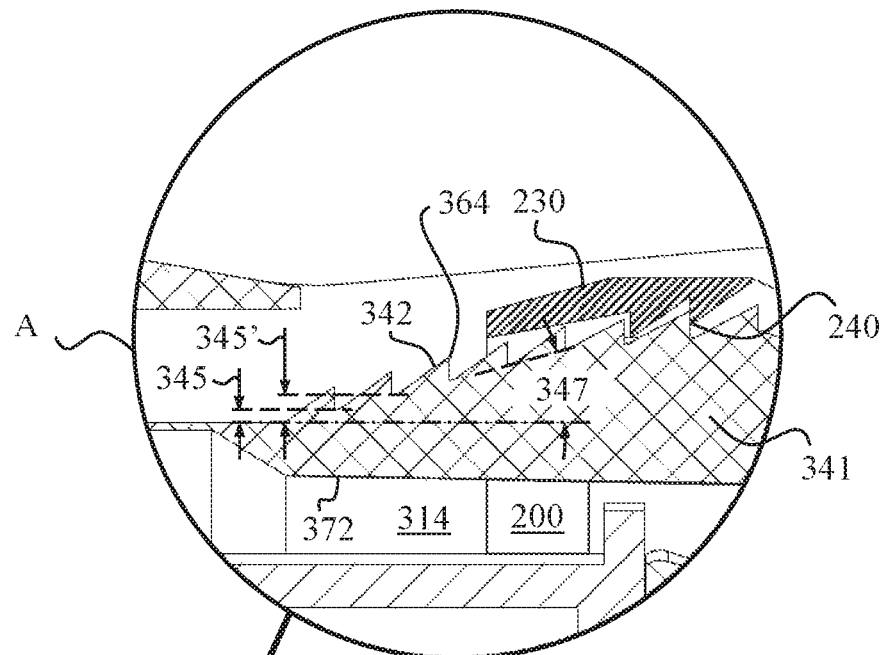
FIG. 7B is an enlarged view showing at least one slider tooth in engagement with at least one ramp tooth.

The housing 300 may define at least a slot 340. In this example, two slots 340 are diametrically disposed on the hub 30. Each slot 340 extends from the first housing opening 312 in the axial direction 304. On either side of the slot 340 is a ramp 341, so that each slot 340 is flanked by a pair of ramps 341. Each ramp 341 is provided with an exterior surface or a ramp face 342 facing away from the hub axis 302. The ramps 341 are provided on an external face of the housing 300 or the hub 30 so that, when the ramps 341 are in engagement with corresponding or respective sliders 230, each slider 230 and respective pair of ramps 341 engage each other outside the first cavity 314. Each ramp is configured with a ramp height 345, 345' that increases (as one travels in the axial direction 304). In other words, each ramp defines an inclination angle 347 with respect to the hub axis 302 (FIG. 7B). The ramp height 345 may increase for a first distance 343, and for convenience, this section of the ramp will be referred to as an "upslope ramp" 346 although it should be understood that this reference is not intended to limit the orientation of the ramp 341 with respect to the ground. The ramp height 345 of the ramp may decrease in the axial direction 304 for a second distance 344. Similarly, for convenience, this section of the ramp is referred to as a "downslope ramp" 347 without intention to limit the orientation of the ramp 341 with respect to the ground. One side of each ramp 341 may be a side wall 348 that serves to define one side of the slot 340. On the other side of the ramp may be a ridge 360 raised above the ramp face 342 by a ridge wall 368. The ridge 360 may be further configured to follow a profile of the ramp or it may be configured with other features. In the example shown, the housing 300 has two symmetrical slots 340 diametrically disposed about the hub axis 302. Each one of the slots 340 is flanked by a pair of ramps 341 and two ridges 360. The two ridges 360 proximal to the same slot 340 may be joined by a bridge 362 near the first end 310 of the housing 300. In some embodiments, the hub includes two slots diametrically disposed on the hub, the two slots extending in the axial direction. The hub further includes two pairs of ramps, each pair of ramps flanking one of the two slots respectively and providing at least one exterior surface to engage with the respective at least one slider.

The ramp face 342 may be configured with at least one ramp tooth 364. In the embodiment shown, a plurality of ramp teeth 364 are provided on the upslope ramp 346. Each one of the ramp teeth 364 protrudes away from the first end 310 of the housing 300. In a preferred embodiment, the upslope ramp 346 is provided with a plurality of ramp teeth 364. Moving in the axial direction 304, it can be seen that each ramp tooth is configured with a greater ramp height 345 relative to its adjacent and preceding ramp tooth. The plurality of ramp teeth 364 thus serves as a series of inclined planes to facilitate movement of the slider 230 in the axial direction 304, while at the same time increasingly pulling the sliders 230 apart and stretching the noose 200. As a result, a single action of pushing the connector 20 deeper into the housing 300 creates at least two simultaneous or concurrent movements in different directions relative to the housing 300, e.g., movement of each slider in a radial direction and in the axial direction. The ramp teeth 364 and the slider teeth 240 are formed as complementary teeth for ratchetly engaging each slider 230 with respective ramps 341. In other words, engagement of at least one slider tooth 240 with at least one ramp tooth 364 prevents the noose 200 from reverting to a less stretched state, and essentially prevents the connector 20 from moving back towards the first end 310 of the housing 300.

Figure 6A:
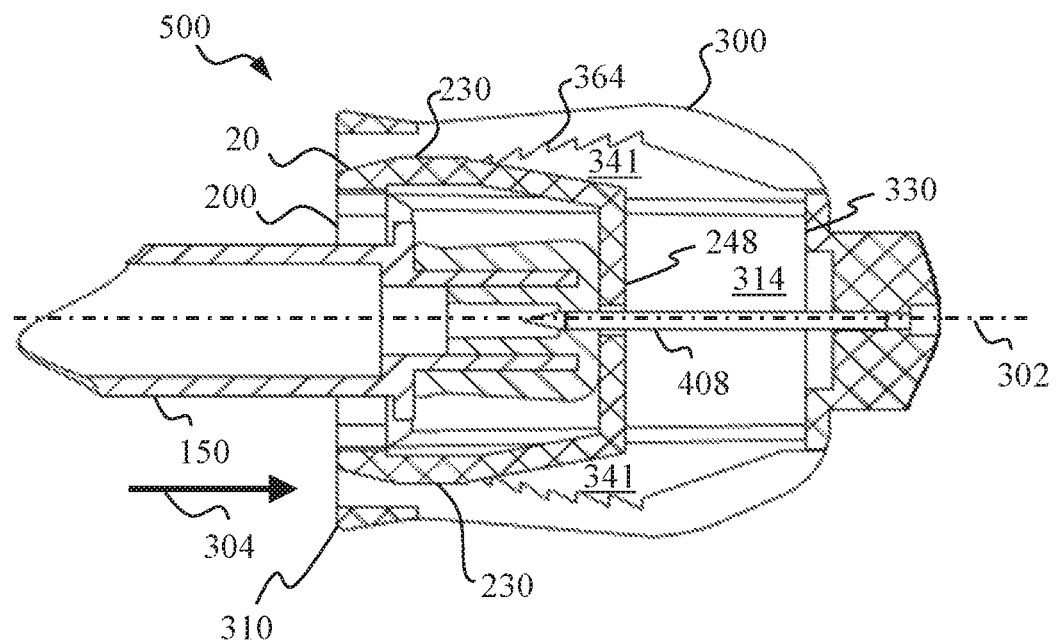
FIG. 6A is a partial cross-section showing the adaptor of FIG. 1 in engagement with a port, in a first configuration.
Figure 6B:
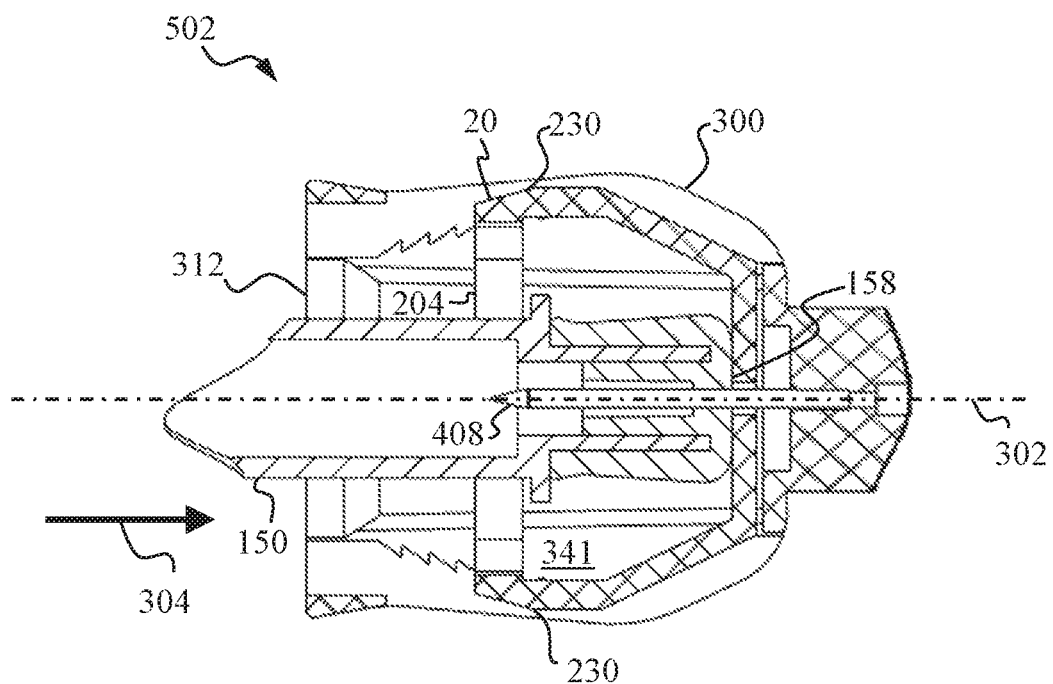
FIG. 6B is a partial cross-section showing the adaptor of FIG. 6A in engagement with a port, in a second configuration.

FIG. 6A shows the connector 20 near the first end 310 of the hub 30, such as when the connector 20 begins to be received by the housing 300. In assembly, the connector 20 can slide in the axial direction 304 relative to the hub 30 for a pre-determined displacement. In so doing, the slider engages the exterior surface 342 while the noose is received by the first cavity 314. In FIG. 6A, the noose 200 of FIG. 4 is disposed within the first cavity 314 while another part of the connector 20 passes through each of the slots 340 to provide the sliders 230 outside the first cavity 314. The elastic or resilient nature of the bands 204 also serves to provide the sliders 230 in biased engagement with the corresponding or respective ramps 341. In particular, the noose 200 is extended diametrically across the first cavity 314 such that each pair of ramps is in biased engagement with a corresponding slider. FIG. 6B shows the connector 20 further away from the first end 310 of the housing 300 or the hub 30 (having moved deeper into the housing 300), such as when the connector 20 has been advanced in the axial direction 304 and further received by the first cavity 314. In transitioning from the first configuration 500 of FIG. 6A to the second configuration 502 of FIG. 6B, the ramps 341 pull the diametrically opposite sliders 230 further apart from each other, stretching the noose 200 diametrically across the first cavity 314 (i.e., diametrically across the hub 30). The resulting tension in the bands 204 of the noose 200 bias the bands 204 towards each other and effect a tighter grip on the port 150. It can be appreciated that the adaptor 10 is configured to increasingly tighten its engagement with the port 150 simultaneously as the connector 20 is advanced in the axial direction 304 relative to the hub 30. At the same time, the noose 200 (or the bands 204) bias the slider teeth 240 against the corresponding ramp teeth 364 (the slider teeth 240 being also caught by the respective ramp teeth 364 in ratchet engagement) so that the connector 20 cannot be moved backwards from the second configuration 502 shown in FIG. 6B to the first configuration 500 shown in FIG. 6A. The sliders 230 and the ramps 341 are configured to ratchetly engage (with the sliders 230 biased against the corresponding ramps 341) so that the connector 20 is prevented from retreating, or moving in a direction opposite to the axial direction 304, relative to the hub 30. This prevents the port 150 from becoming disengaged from the hub 30 and prevents exposing the port septum 158. The adaptor 10 thus ensures that the port septum 158 is not exposed to the user or the environment once the port 150 is received by the hub 30 along with the connector 20. In use, the noose 200 serves to provide radially directed biasing forces to tighten the ratchet engagement between the connector 20 and the hub 30, as well as simultaneously tighten the coupling of the port 150 with the adaptor 10.

Figure 7A:
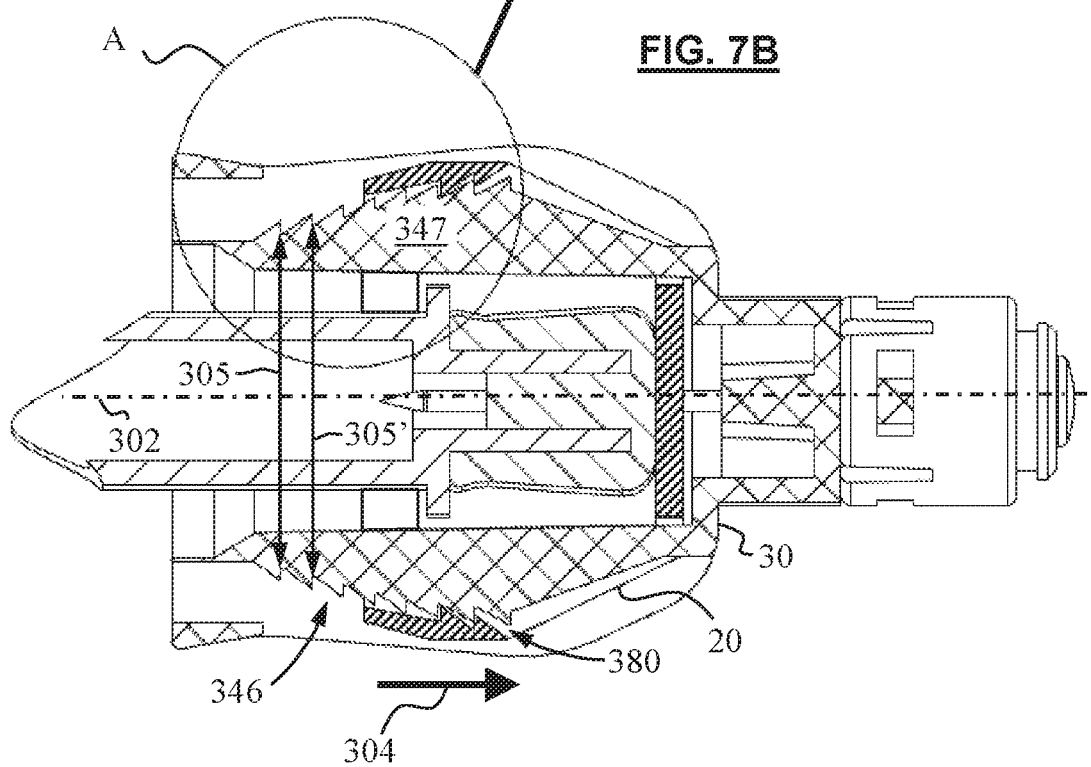
FIG. 7A is a partial cross-section of the adaptor according to one embodiment of the present disclosure.

Alternatively described, in a first configuration 500, the connector 20 is disposed with the noose 200 partially received by the first cavity 314 and the sliders 230 near the first end 310 of the hub 30, as shown in FIG. 6A. A second configuration 502, after the connector 20 has moved in the axial direction 304 relative to the hub 30, is shown in FIG. 6B. The bands 204 of the connector 20 are inside the first cavity 314 with the necks 210 passing through the slots 340 so that the slides 230 are outside the first cavity 314. The connector 20 is thus partially received by the first cavity 314, with the noose 200 disposed or received in the first cavity 314, and with the sliders 230 outside the hub 30. Each of the sliders 230 has an interface 232 abutting or engaged with the respective ramps 341. The connector 20 is resiliently deformable so that the sliders 230 are in biased engagement with the ramps 341 with the sliders 230 hooked over the ramps 341, as illustrated in FIG. 7A and FIG. 7B. More specifically, the slider teeth 240 are in biased engagement with the respective ramp teeth 364. In the example shown, at least one of the slider teeth 240 serves as a pawl in biased engagement with the ratchet provided by the respective ramp teeth 364. The upslope ramp 346 may be inclined at an acute angle relative to the hub axis 302.

The adaptor 10 may be used to conveniently and more safely introduce a fluid, such as a medication or other substances, into a fluid bag. Referring again to FIGS. 6A and 6B, a user may hold the adaptor 10 with one hand and slip the first housing opening 312 over the port 150 in one movement. This simultaneously brings the port 150 through the opening 202 between the bands 204. Continuing the same movement can further bring the port septum 158 into abutment with the base 248 of the connector 20. The hub 30 includes a needle 408 axially disposed therein. It can be appreciated that the same movement can bring the needle 408 to pierce through the port septum 158. The connector 20 may also be made to advance in the axial direction 304 relative to the housing 300 until the base 248 is prevented from travelling further by the divider 330. Moving the connector 20 in the axial direction 304 relative to the housing 300 will also move the terminal 151 of the port 150 along with the connector 20, since the noose of the connector 20 is coupled to the port 150. In other words, when the port 150 is coupled with the noose 200, in moving the connector 20, the port septum is presented by the noose 200 in the first cavity 314, and the port septum is a position to receive the needle. When the port septum is pierced by the needle 408, fluid communication between the second cavity 324 and the port 150 is established. Fluid communication between the first cavity 314 and the second cavity 324 is thus solely via the needle 408.

The user may exert a force on an exposed part of the connector 20 to move the connector 20 in the axial direction 304 relative to the housing 300. The exposed part of the connector 20 can be one or more of the sliders 230. The exposed part of the connector 20 may include one or more of the tab surfaces 238. A thumb of the hand holding the adaptor 10 can push on a tab surface 238 while the other fingers of the same hand hold the housing 300. The user can thus fit the adaptor 10 to a port 150 using a one-hand operation.

Simultaneous with the connector 20 being moved in the axial direction 304 relative to the housing 300, the connector 20 is increasingly deformed as the sliders 230 travel along the upslope ramps 346. As the sliders 230 are moved further along the axial direction 304, they are increasingly displaced from the hub axis 302 because of the increasing diameter or increasing radial dimension 305, 305' of the housing 300 in the axial direction 304. The ramp height 345 may contribute to the increasing diameter or increasing radial dimension 305, 305' of the housing 300 in the axial direction 304. In other words, with at least one ramp extending in the axial direction 304, and the exterior surface 342 being disposed on the at least one ramp 346, the connector 20 is increasingly deformed as the connector 20 is displaced in the axial direction 304 relative to the hub 20. As shown in FIG. 7A and FIG. 7B, there may be provided at least one slider tooth 240 configured to engage respective complementary ramp teeth 364. Each slider 230 may be provided with two slider teeth 240 configured to engage a row of ramp teeth 364 on one of the ramps 341. As the sliders 230 travel along the respective upslope ramps 346, the sliders 230 are simultaneously forced further apart from one another, resulting in the bands 204 being biased toward one another and thereby clamping the port 150 in between. The noose 200 thus resiliently conforms about the port 150 and secures the port 150 against de-coupling from the adaptor 10.

The user can easily confirm that the port 150 has been securely coupled to the adaptor 10 by attempting to tug the port 150 away from the adaptor 10 (for example, by pulling on the port 150 in a direction substantially opposing the axial direction 304). If the port 150 has been securely coupled to the adaptor 10, the sliders 230 and the respective ramps 341 will be ratchetly engaged so that the connector 20 cannot be moved in a direction opposite to the axial direction, relative to the hub 30. The noose 200 will also be stopped by the ledge 159 if external forces tend to pull the port 150 away from the adaptor 10 or if the port exhibits a tendency to slip free of the noose 200.

In another aspect, the adaptor 10 includes a hub 30 and a connector 20. The hub 30 includes a ramp face or an exterior surface 342 and an interior surface 372, with the interior surface 372 defining a first cavity 314. The connector 20 is partially receivable in the first cavity 314. The exterior surface 342 is configured to enable slidable engagement with the connector 20 in an axial direction 304. The exterior surface 342 is further configured to limit movement of the connector 20 in a second direction relative to the hub, the second direction substantially opposing the axial direction 304. The connector 20 includes a noose 200 which can also serve as a biasing element. The connector 20 includes at least one slider 230 coupled to the noose 200. The at least one slider 230 is configured to engage the exterior surface 342 such that the noose 200 is received by the first cavity 314. In other words, the noose 200 is receivable into the first cavity 314.

The exterior surface 342 of the hub 30 provides two sets of ratchets (ramp teeth) 364. The connector 20 includes two sets of pawls (slider teeth) 240 diametrically disposed on the biasing element 200. In assembly, each set of pawls 240 can come to rest in biased engagement with a corresponding set of ratchets 364, with the bias provided by elastic deformation of the noose or the biasing element 200. The noose 200, when elastically deformed to extend diametrically across the first cavity, biases each set of pawls 240 against the corresponding set of ratchets 364.

The connector 20 is configured for ratchet-and-pawl coupling 380 with the exterior surface 342 of the hub 30. The exterior surface 342 includes an inclined surface 346. The inclined surface 346 defines an inclination angle 347 relative to a hub axis 302 of the hub 30. In some embodiments, the inclined surface 346 may define an inclination angle 347 relative to the interior surface 372 of the hub 30. In other words, the exterior surface 342 (or the inclined surface 346) is configured to enable slidable engagement of the connector 20 with the hub 30 with the connector moving in a first direction (the axial direction 304) relative to the hub 30, and to limit movement of the connector 20 relative to the hub 30 in a second direction (substantially opposite the axial direction 304).

In some embodiments, the exterior surface 342 includes a plurality of inclined planes (ramp teeth) 364 disposed thereon, such that the exterior surface 342 facilitates sliding movement of the connector 20 relative to the hub 30, in which the sliding movement is substantially in the first direction 304. The plurality of inclined planes 364 are arranged to provide limitation to a movement of the connector 20, relative to the hub 30, in the second direction (substantially opposing the first direction 304). The plurality of ramp teeth 364 are disposed along the inclined surface 346 of the exterior surface 342, such that at least two of the plurality of ramp teeth 364 are disposed at different and increasing ramp heights 345, 345'. In some embodiments, the at least two of the plurality of ramp teeth 364 are disposed at different and increasing radial displacements 305, 305'.

Figure 8:
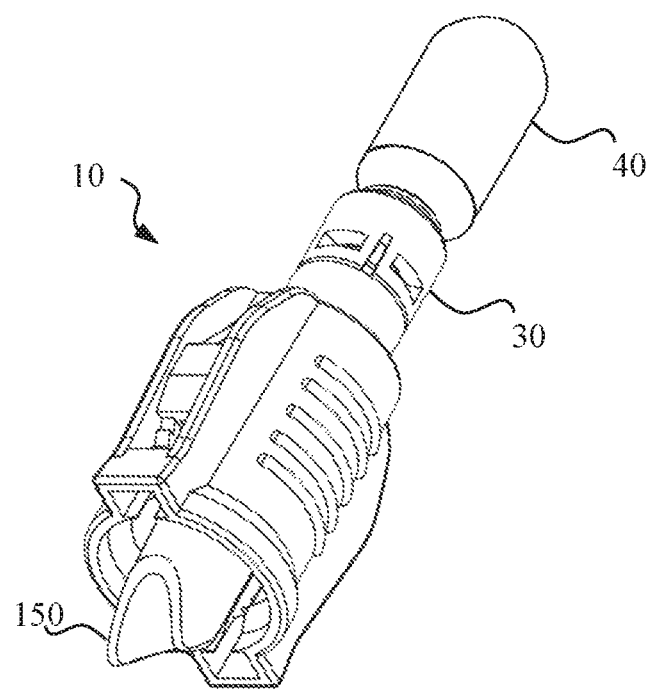
FIG. 8 is a partial perspective view of an adaptor coupled with a delivery system and a port.

The user may engage a delivery system 40, which may include a syringe or an actuating apparatus, with the second end 320 of the hub 30, so as to deliver medication from the delivery system 40 to the fluid bag. As shown in FIG. 8, the syringe of the delivery system 40 may include a compatible connecting interface for coupling with the second end 320 of the hub 30, such that fluid communication is established between the delivery system 40 and the hub 30.

Figure 9:
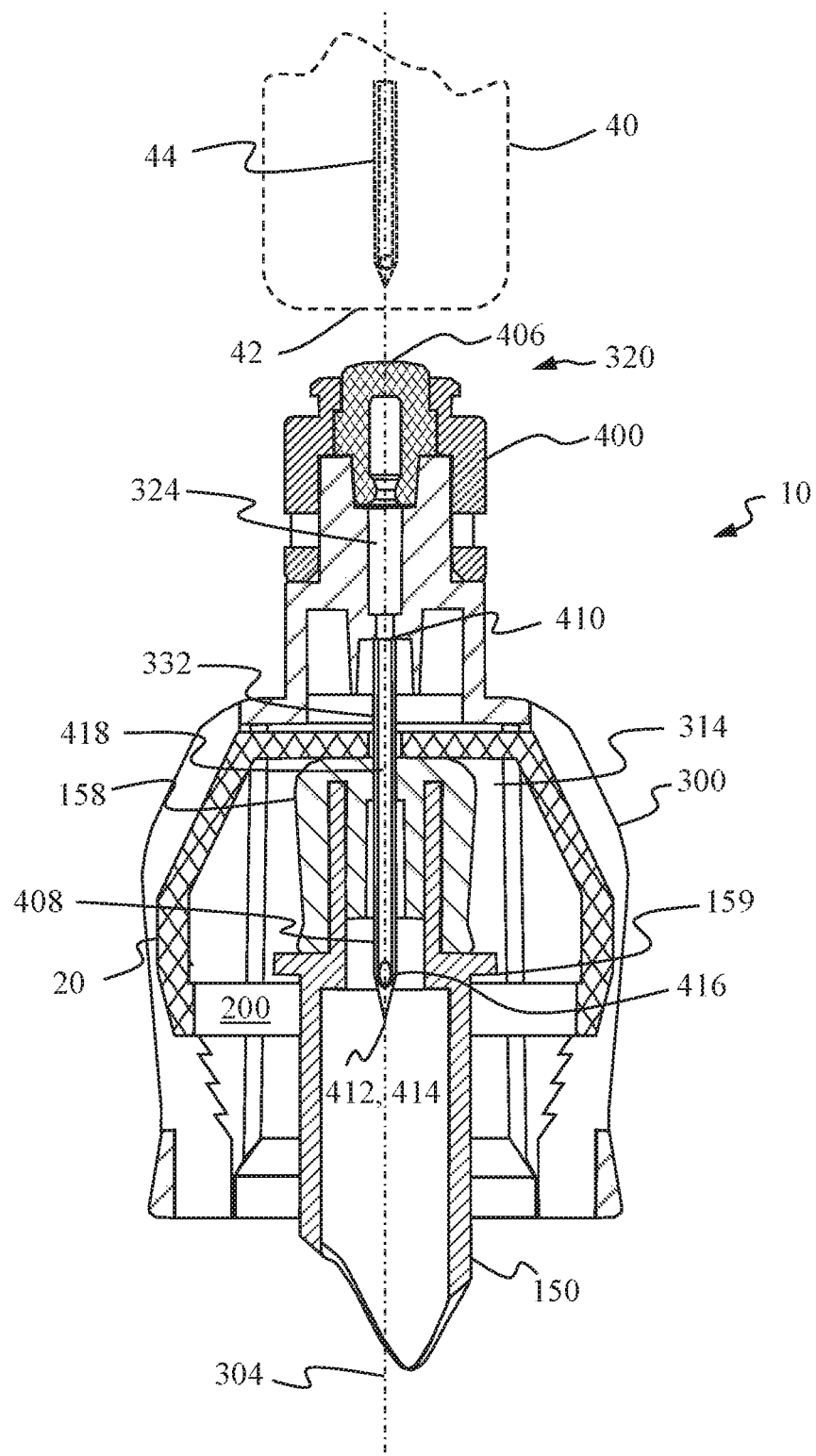
FIG. 9 is a partial cross-sectional view illustrating a fluid communication path provided by an adaptor of the present disclosure.

The hub 30 may further include a needle 408 disposed in the hub 30. As shown in FIG. 9, the needle 408 includes a proximal end 410 and a distal end 412. The needle 408 may be disposed substantially parallel to the axial direction 304, such that it is supported by the divider aperture 332 with its proximal end 410 in the second cavity 324 and its distal end 412 is in the first cavity 314 of the housing 300. The needle 408 is provided with a tip 414 at the distal end 412, so that the needle 408 may break or pierce a port septum 158. One or more holes 416 near the tip 414 opens to an internal passage 418 within the needle 408. When the delivery system 40 is coupled via a compatible connecting interface 42 to the second end 320 of adaptor 10, a delivery system needle (such as a retractable needle) 44 of the delivery system 40 may be provided to pierce the hub septum 406. The hub septum 406 may include a self-sealing septum configured to provide an effective mechanical barrier to leakages or contamination, despite repeated punctures by the delivery system needle 44. It can be appreciated that the adaptor 10 is suitable for use as a closed system transfer device (CSTD) such that fluid communication can be provided from the delivery system 40, via the compatible connecting interface (e.g., through the delivery system needle 44), via the second cavity 324, through the proximal end of the needle 410, via the internal passage of the needle 418, through the one or more holes 416 of the needle, and via the port 150 to the fluid bag.

In one embodiment, the connector 20 is suitable for being coupled to the port 150 before the connector 20 is engaged to the housing 300. The connector 20 has at least one slider 230 which can also function as a guide as the slider 230 is passed under one bridge 362 of the housing 300. As shown in FIG. 6A, the needle 408 can be presented to pierce the port septum 158. When the connector 20 is moved in the axial direction 304 relative to the housing 300, the distal end 412 of the needle 408 is disposed deeper in the port 150, as shown in FIG. 6A. Fluid communication between the port 150 and the delivery system 40 is made possible via each hole 416 and the internal passage 418 of the needle 408. With fluid communication established between the fluid bag and the delivery system 40, medication in the delivery system 40 can be delivered to the fluid bag.

In another embodiment, the connector 20 is suitable for being coupled to the housing 300 before the connector 20 is engaged with the port 150. The noose 200 is configured to provide an opening of a size suitable to receive the terminal 151 of a port 150 therethrough. If the port 150 includes a flange 153, the opening 202 is preferably sized to allow the flange 153 to pass through the noose 200 so that the flange 153 is disposed between the bands 204 and the base 248, as shown in FIG. 6A. As the connector 20 is made to progress in the axial direction 304 relative to the housing 300, the connector 20 is deformed so that the connector 20 tightens around the port 150. The connector's axial displacement relative to the housing 300 may be concurrent with the sliders 230 being increasingly radially displaced by the ramps 341 and the bands 204 increasing in length. The deformation undergone by the connector 20 may include the noose 200 changing in its radius of curvature 226. The noose 200 may change from a larger radius of curvature 226 to a smaller radius of curvature 226 as it resiliently deforms to fit around the port 150. As shown in FIG. 6A, the needle 408 can pierce the port septum 158 as the port 150 is received by the adaptor 10. When the connector 20 is moved in the axial direction 304 relative to the housing 300, the distal end 412 of the needle 408 is disposed deeper in the port 150, as shown in FIG. 6A. Fluid communication between the port 150 and the delivery system 40 is made possible via the hole 416 and the internal passage 418 of the needle 408. With fluid communication established between the fluid bag and the delivery system 40, medication in the delivery system 40 can be delivered to the fluid bag.

In any of the embodiments described, it can be appreciated that a change from the first configuration 500 to the second configuration 502 can be brought about by using one hand in essentially one movement of moving the connector 20 relative to the hub 30 in the axial direction 304.

The adaptor 10 can promote improved safety in the filling of fluid bags in various ways, even when used with various non-closed system transfer devices. Still referring to FIG. 9, if the delivery system includes a syringe 40 with a syringe needle 44, the syringe needle 44 can pierce the hub septum 406 to provide fluid communication between the syringe 44 and the port 150. When the syringe needle 44 is drawn out of the adaptor 10, the hub septum 406 in effect "wipes" the syringe needle 44 clean by the time the tip or opening of the syringe needle 44 disengages from the hub septum 406. Any droplet or trace substances would have been retained on the interior side of the hub septum 406 and kept within the adaptor 10. The hub septum is made of an elastomeric material that "self-heals" so that the second end 320 of the adaptor provides a sealed mechanical barrier, preventing leakage or contamination of/by substances such as hazardous drugs or biological substances. The same adaptor is useful in both closed and non-closed systems.

Another example will be described with the aid of FIGS. 10A to 10D. FIG. 10A shows an injector 600 as an example of a closed system transfer device. The injector 600 includes a luer lock end 604 and a receiving end 602. The luer lock end 604 can be coupled to corresponding luer lock syringe 610 to adapt the syringe for use as a closed system transfer device. A vial 630 of drug or other substances may be fitted with a vial adaptor 620 so as to adapt the vial for use in a closed system. When the receiving end 602 of the injector is coupled to a port opening 622 of the vial adaptor 620, contents of the vial 630 may be drawn into the syringe 610 (FIG. 10B). FIG. 10C shows a fluid bag 710 with one of its ports 150 provided with an adaptor 10 according to one embodiment of the present disclosure. After de-coupling the vial adaptor 620 from the injector 600, the receiving end 602 of the injector 600 may be coupled to the second end 320 of the adaptor 10. The substance in the syringe 610 can thus be safely transferred via the adaptor 10 into the fluid bag 710 in a manner compliant with applicable safety regulations, such as regulations for the safe handling of hazardous drugs. As shown in FIG. 10D, even when the injector 600 is removed, the adaptor 10 remains secured to the fluid bag 710. As described above, the adaptor 10 cannot be detached from the fluid bag 710 once the two are securely coupled to one another.

FIG. 11 shows another embodiment of a fluid transfer system 700. The fluid transfer system 700 can be adapted for use in CSTD-complaint procedures or environments. The fluid transfer system includes a fluid bag 710 with a port coupled with an adaptor 10'. As described above with the aid of FIGS. 10A to 10D, the fluid transfer system enables the fluid bag to be filled—even in an open ward—without subjecting the healthcare professional or the patient to the risk of an exposed needle. The hub septum 406 of the adaptor 10' continues to provide an effective mechanical barrier against leakage or exposure of the fluid in the fluid bag to the external environment, after the fluid bag has been filled. The other port of the fluid bag 710 can also be coupled with an adaptor 10. In this example, the adaptor 10 can be coupled with a fluid bag tubing 720 with the aid of CSTD-compliant injectors 600 so that neither the healthcare professional nor the patient is at risk from an exposed needle at any time. After the fluid bag 710 has been emptied of its contents, the adaptor 10 secured on the port serves as a clear indicator that the fluid bag 710 has been used. This guards against unintentional re-use of the fluid bag 710. The needle 408 within the adaptor 10 is not exposed to the environment at any time. Since the needle 408 is not drawn out through the broken port septum 158, there is little likelihood for trace medication to appear on the port septum 158. Additionally, the broken port septum 158 is abutted by the base 248 of the connector 20 and not exposed. If the hub septum 406 is pierced by a needle or a spike, and the needle or spike is subsequently removed, the needle or spike will be cleaned by the interior surface of the hub septum such that no trace substances will be exposed to the outer surface of the adaptor or the needle (or spike). Additionally, the hub septum 406 will re-seal itself to again provide an effective mechanical barrier to leakage or contamination.

In one aspect, the adaptor 10 provides for the port septum 158 to be pierced open to establish a desired fluid communication without exposing the user to the needle 408 at any time during the process of filling the fluid bag 710. There is therefore reduced possibility that the user will be accidentally pricked by an exposed needle and risk exposing broken skin to the medication being delivered to the fluid bag. In another aspect, since the connector 20 cannot reverse its direction of travel relative to the hub 30, the port septum 158 is never drawn out from the housing. The adaptor 10 can be part of a fluid transfer system 700 which includes a fluid bag 710 having a port 150 sealed or sealable with a port septum 158. The adaptor 10 includes a hub 30 defining a first cavity 314 and a second cavity 324, the second cavity 324 extending from a divider 330 to an opposing end 321. The opposing end 321 is sealable by a hub septum 406. The adaptor 10 includes a needle 408 that is disposed in the hub at the divider 330. The adaptor 10 further includes a connector 20 having a noose 200, the noose 200 being configured to couple the port 150 and to present the port septum 158 in the first cavity 314 for piercing by the needle 408, such that fluid communication between the port 158 and the second cavity 324 is solely via the needle 408. In this manner, a dry-seal can be established for the port 150 of the fluid bag 710.

The noose 200 in resilient engagement with the tube 152 of the port 150 can act against accidental de-coupling of the port 150 from the connector 20, thus reducing likelihood of spillage or leakage. In some cases, a resistance to de-coupling is reinforced by interference from the ledge 159. The pawl-and-ratchet engagement between the slider teeth 240 and the ramp teeth 364 additionally locks the coupling of the connector 20 (and hence the port 150) with the hub 30. The resulting vise grip makes the adaptor 10 difficult (if not practically impossible) to remove from the fluid bag 710. The noose 200 is configured to bias the connector 20 in ratchet engagement with the hub 30 against de-coupling of the adaptor 10 and the port 150 when the second cavity and the port 150 are in fluid communication. The adaptor 10 cannot be easily or accidentally removed after the fluid bag 710 has been filled with medication or other substances. This means that the port septum 158 is never exposed to the user. An attached adaptor 10 can therefore also serve as a highly visible identifier for fluid bags already filled or used, and prevent improper re-filling or re-use of the fluid bags. Contamination and such safety-related issues can thus be circumvented.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be effected therein by one skilled in the art without departing from the scope or spirit of the disclosure.

The invention claimed is:

1. An adaptor comprising:
   a hub having an exterior surface and an interior surface, the interior surface defining a first cavity; and
   a connector, the connector including:
      first and second bands defining a variable opening configured to couple a port; and
      at least one slider coupled to the first and second bands, the first and second bands being receivable by the first cavity when the at least one slider engages the exterior surface, wherein the first and second bands are configured to tighten a coupling with the port.

2. The adaptor according to claim 1, wherein the connector is elastically deformed by engagement of the at least one slider with the exterior surface such that the at least one slider is biased against the exterior surface.

3. The adaptor according to claim 2, wherein the hub further comprises at least one ramp extending in an axial direction, the exterior surface being disposed on the at least one ramp such that the connector is increasingly deformed as the connector is displaced in the axial direction relative to the hub.

4. The adaptor according to claim 3, wherein the at least one slider and the exterior surface are configured to ratchetly engage with one another to prevent movement of the connector relative to the hub in a direction substantially opposing the axial direction.

5. The adaptor according to claim 4, wherein the hub further defines a second cavity, the second cavity extending from a divider to an opposing end, wherein the second cavity is in fluid communication with the first cavity at the divider, and wherein the second cavity is sealable at the opposing end by a hub septum.

6. The adaptor according to claim 5, wherein the adaptor further comprises a needle axially disposed in the hub, and wherein fluid communication between the first cavity and the second cavity is solely via the needle.

7. The adaptor according to claim 6, adapted for use with a fluid bag having the port, the port being coupled with a port septum, wherein the first and second bands are configured to elastically couple the port and to position the port septum in the first cavity for piercing by the needle, such that fluid communication between the second cavity and the port is solely via the needle.

8. The adaptor according to claim 2, wherein the hub comprises:
   two slots diametrically disposed on the hub and extending in an axial direction; and
   two pairs of ramps, each pair of ramps flanking one of the two slots respectively, wherein the exterior surface is disposed on the pairs of ramps.

9. The adaptor according to claim 8, wherein the connector is increasingly deformed as the connector is displaced in the axial direction relative to the hub.

10. The adaptor according to claim 8, wherein the exterior surface comprises a plurality of ramp teeth disposed at increasing ramp heights, the plurality of ramp teeth being configured to ratchetly engage with a corresponding slider to prevent movement of the connector relative to the hub in a direction substantially opposing the axial direction.

11. The adaptor according to claim 8, wherein the connector further comprises two sliders, wherein the connector is deformable by the first and second bands being extended diametrically across the first cavity such that each pair of ramps is in biased engagement with a corresponding slider.

12. The adaptor according to claim 11, wherein the hub further defines a second cavity, the second cavity extending from a divider to an opposing end, wherein the second cavity is in fluid communication with the first cavity at the divider, and wherein the second cavity being sealable at the opposing end by a hub septum.

13. The adaptor according to claim 12, wherein the adaptor further comprises a needle axially disposed in the hub, and wherein fluid communication between the first cavity and the second cavity is solely via the needle.

14. The adaptor according to claim 3, wherein the at least one slider rides along the at least one ramp, which increases tension in the first and second bands, thereby further tightening the coupling with the port.

15. The adaptor according to claim 14, wherein the at least one slider comprises a first slider attached to respective first ends of the first and second bands, and a second slider attached to respective second ends of the first and second bands that are opposite the first ends.

16. The adaptor according to claim 15, wherein the at least one ramp comprises a first ramp and a second ramp opposite the first ramp, and the first and second sliders ride along the first and second ramps to further tighten the coupling with the port.

17. The adaptor according to claim 15, wherein the first and second sliders and respective exterior surfaces of the first and second ramps are configured to ratchetly engage with one another to prevent movement of the connector relative to the hub in a direction substantially opposing the axial direction.

* * * * *